United States Patent [19]
Wing

[11] Patent Number: 5,527,295
[45] Date of Patent: Jun. 18, 1996

[54] GRAVITATIONAL, MAGNETIC, FLOATING BALL VALVE

[76] Inventor: Michael L. Wing, 26234 Windsor St., Loma Linda, Calif. 92354

[21] Appl. No.: 392,192

[22] Filed: Feb. 22, 1995

[51] Int. Cl.⁶ .................................................. A61M 5/00
[52] U.S. Cl. ............................................ 604/254; 604/255
[58] Field of Search ................................ 604/254, 255, 604/253, 252, 65, 247

[56] References Cited

U.S. PATENT DOCUMENTS

| | | |
|---|---|---|
| 2,786,467 | 3/1957 | Price ........................................ 604/255 |
| 4,037,596 | 7/1977 | LeFevre et al. . |
| 4,038,981 | 8/1977 | LeFevre et al. . |
| 4,038,982 | 8/1977 | Burke et al. . |
| 4,103,686 | 8/1978 | LeFevre . |
| 4,519,792 | 5/1985 | Dawe et al. ............................. 604/152 |
| 4,525,163 | 6/1985 | Slavik et al. ............................. 604/65 |
| 4,551,134 | 11/1985 | Slavik et al. ............................. 604/67 |
| 4,708,831 | 11/1987 | Elsworth et al. ...................... 261/130 |

FOREIGN PATENT DOCUMENTS 2012228  9/1971  Germany .............................. 604/254

*Primary Examiner*—John D. Yasko
*Attorney, Agent, or Firm*—Richard C. Litman

[57] ABSTRACT

A gravitational, magnetic, floating ball valve for use in the medical field as a protective fluid cut-off valve when medicine and/or fluids are infused intravenously in patients. The ball valve can be inserted in either an intravenous line, a dosage meter tube or inside an intravenous supply bag and in combinations thereof.

13 Claims, 4 Drawing Sheets

GRAVITATIONAL, MAGNETIC, FLOATING BALL VALVE

BACKGROUND OF THE INVENTION

1. Field of the Invention

The present invention relates to ball valves useful in the medical industry for installation in either an intravenous bag, intravenous line or a dosage meter.

2. Description of the Prior Art

During hospitalization, a patient's body fluids must be replenished by infusion in order to maintain certain levels of body fluids. The nurse must monitor the addition of body fluids such as Ringer's Solution, blood plasma, sucrose solution, glucose solution, saline solution, etc., in order to prevent the entrapment of air in the solutions when the supply of infusion fluid is exhausted. When air is allowed to enter the patient's blood stream as air emboli, serious conditions such as infarction of the heart and/or brain may result. Therefore, the present inventor has devised a simplified ball valve system to enable hospital personnel to observe the depletion of the infusion fluid and prevent such problems. When the fluid is about to be exhausted, this invention would automatically cut-off the fluid supply, thereby preventing entrapment of air in the body fluid being infused. No complicated machinery is required as disclosed by the following prior art.

Examples of complicated intravenous infusion control devices are illustrated by the following patents. In U.S. Pat. Nos. 4,551,134 and 4,525,163, issued on Nov. 5, 1985 and Jun. 25, 1985, respectively, to William H. Slavik et al., a magnetically responsive ball is displaced from its fluid stopping position by an electromagnet programmed by a micro-computer to initiate a drip-dropping schedule.

In U.S. Pat. No. 4,519,792 issued on May 28, 1985, to Garfield A. Dawe, an infusion pump system contains a removable cassette including two magnetically biased valves at each end with externally mounted magnets monitored within prescribed pressure limits by a micro-computer to control fluid flow.

In U.S. Pat. No. 4,038,981 to Robert J. LeFevre et al. and U.S. Pat. No. 4,038,982 to George K. Burke et al., both issued on Aug. 2, 1977, an electronically controlled, gravity-feed, intravenous infusion set which controls drops of fluid by dislodging a ball of unknown composition by either an electromagnet or a permanent magnet is disclosed. An essential component of this system is a computerized photometric system which controls the drop frequency.

In U.S. Pat. No. 4,037,596 issued on Jul. 26, 1977, to Robert J. LeFevre et al., a drop by drop parenteral administration set with an internal valve containing a steel ball and a flow restrictor which limits and actuates the ball valve is disclosed. No magnetic control is contemplated.

In U.S. Pat. No. 4,103,686 issued on Aug. 1, 1978 to Robert J. LeFevre, a dual valve assembly for dual intravenous infusions for controlling both forward and reverse flow through a flow line is disclosed. The valve ball is controlled by an external electromagnet (and a drop frequency controller) which when energized displaces the valve ball from its closing position. The second valve member is a disc which normally closes off the gravity fed fluid, and the disc is dislodged by energizing the valve ball to move it and a third fluted actuating rod to push up the disc and commence feeding of the fluid.

Finally, U.S. Pat. No. 4,708,831 issued on Nov. 24, 1987 to Adrian J. Elsworth et al. discloses a water humidifier which dispenses water through a removable drop counter containing a magnetically actuated steel ball valve. The electromagnet is controlled by a micro-processor to displace the steel ball slightly from its closing position and permit water flow.

None of the above inventions and patents, taken either singly or in combination, is seen to describe the instant invention as claimed.

SUMMARY OF THE INVENTION

The present invention is a gravitational, magnetic, floating ball valve for use in stopping the flow of body fluids in intravenous infusion in order to prevent embolism in the patient undergoing infusion. This device can be used inside an intravenous (IV) bag, an IV tube and/or a dosage meter, i.e, either separately or in a combination. The ball valve comprises two magnets arranged to attract each other to close off the flow of infusion fluid. The upper or upstream magnet is encased in either a hollow or solid plastic ball which seats either on a lower or downstream cup-shaped or flat magnet when the fluid level drops. The downstream magnet can be sealed in material such as rubber or have a surface layer of plastic. The floating ball can be encased further in a plastic or metal mesh cylinder when the ball is utilized inside an IV bag or a dosage meter. To enhance the visibility of the floating ball, it can be brightly colored. Since no external energization of the magnets is required, this floating ball valve is economical and simple to operate. The ball valve can be autoclaved and reused if desired.

Accordingly, it is a principal object of the invention to provide an economical, reusable gravitational, magnetic, floating ball valve comprising two magnets of dissimilar shape.

It is another object of the invention to provide a magnetic ball valve which does not require external energization.

It is a further object of the invention to provide a floating ball as part of the valve system which can be either hollow or solid.

Still another object of the invention is to provide use of the floating ball valve system in either an IV bag, IV tube or a dosage meter and combinations thereof.

It is yet another object of the invention to provide a cage for the floating ball when disposed in an IV bag and a dosage flowmeter.

It is a final object of the invention to provide a lower (downstream) magnet shaped as either a disc or a cup having an aperture enabling fluid flow.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
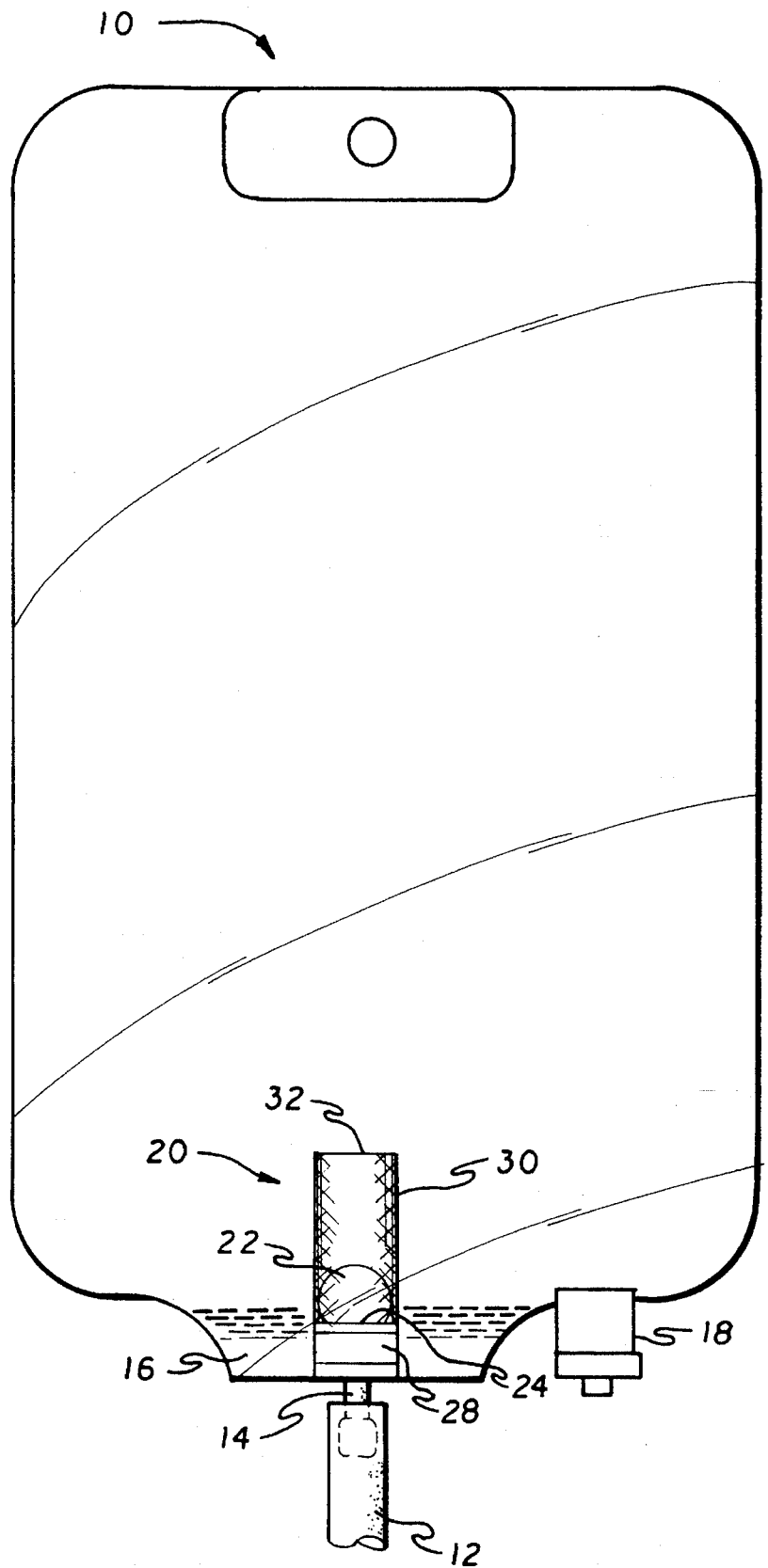
FIG. 1 is an environmental front elevational view of a first embodiment of the gravitational, magnetic, floating ball valve unit inside an IV bag.

The present invention is adapted for use in an intravenous (IV) bag as illustrated in FIG. 1. An IV bag assembly 10 having an IV tube 12 at IV port 14 is normally positioned to release its contained body fluid 16 (filled through filler port 18) through the IV tube 12 to a patient via a needle (not shown). If the entire contents of the bag is intended for infusion, applicant's gravitational, magnetic, floating ball valve unit 20 is inserted in the IV bag 10 before a body fluid 16 is added. Alternatively, the IV bag 10 assembly can have the floating ball valve unit 20 inserted during fabrication of the bag assembly 10.

Figure 2:
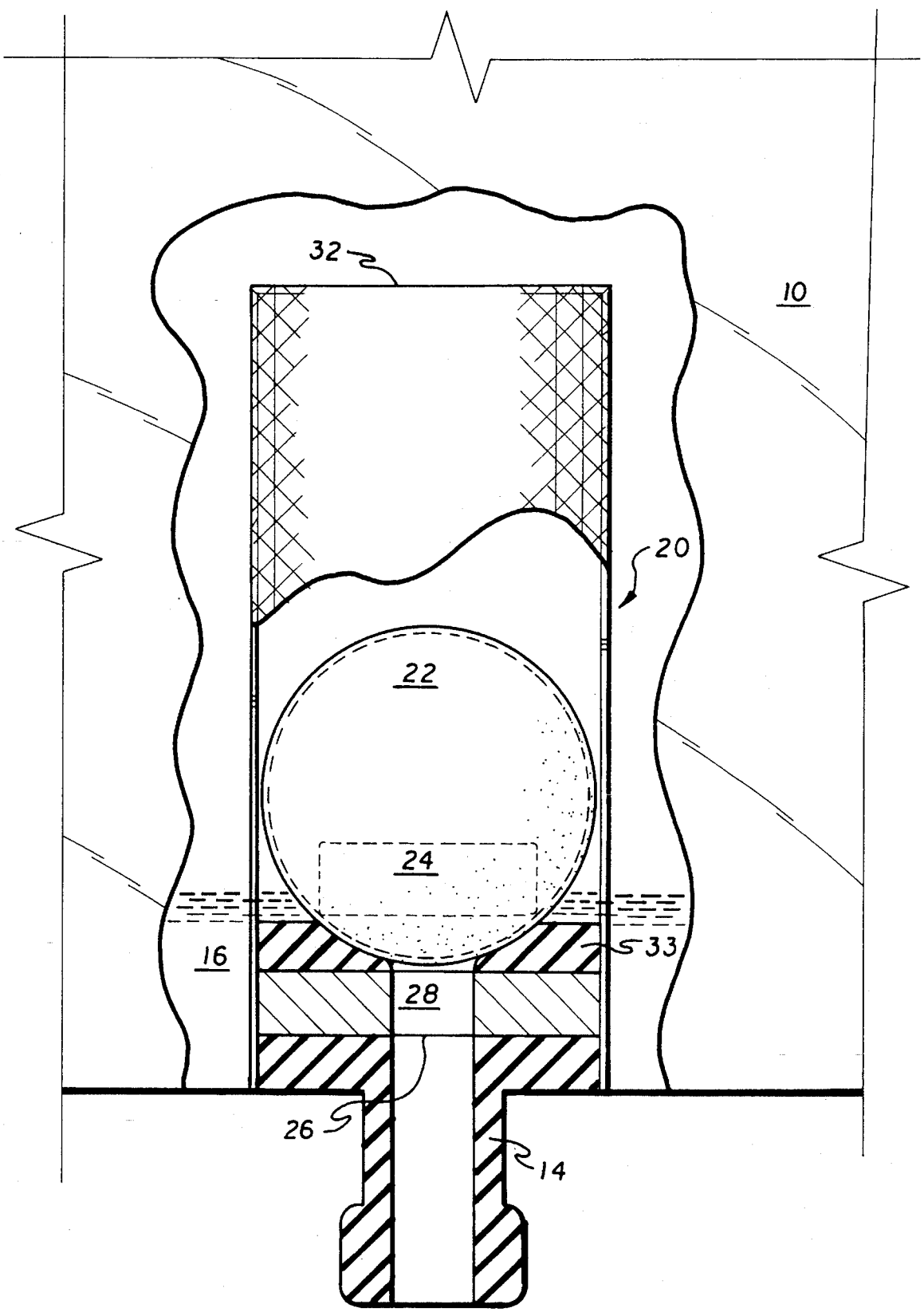
FIG. 2 is a partially sectioned and enlarged scale side view of a ball valve seated on a flat downstream magnet.

In FIG. 2, an enlarged view of the first embodiment of the ball valve unit 20 is illustrated. In this figure, a hollow ball 22 containing a magnet 24 (which can be of any shape) is positioned upstream to close off the supply of fluid 16 by sealing the aperture 26 in the downstream magnet 28 which is a flat disc in this embodiment. The ball 22 and the flat magnet 28 are encased inside a tubular cylinder 30 having a cap 32. The tubular cylinder 30 is made of mesh material consisting of stainless steel or a clear plastic composition. The magnet 24 is preferably set (immobilized) inside the hollow ball 22, but can be freely mobile. The hollow ball 22 can be brightly colored such as in pink or yellow. This coloring would allow the attendant to readily determine whether the hollow ball 22 is floating or resting on the lower or downstream magnet 28. The hollow ball 22 seats on a thin apertured silicone liner 33 which enhances the effective sealing of the aperture 26 in the flat downstream magnet 28 when the level of the body fluid 16 falls proximate to the surface of the downstream magnet 28 and liner 33.

Figure 3:
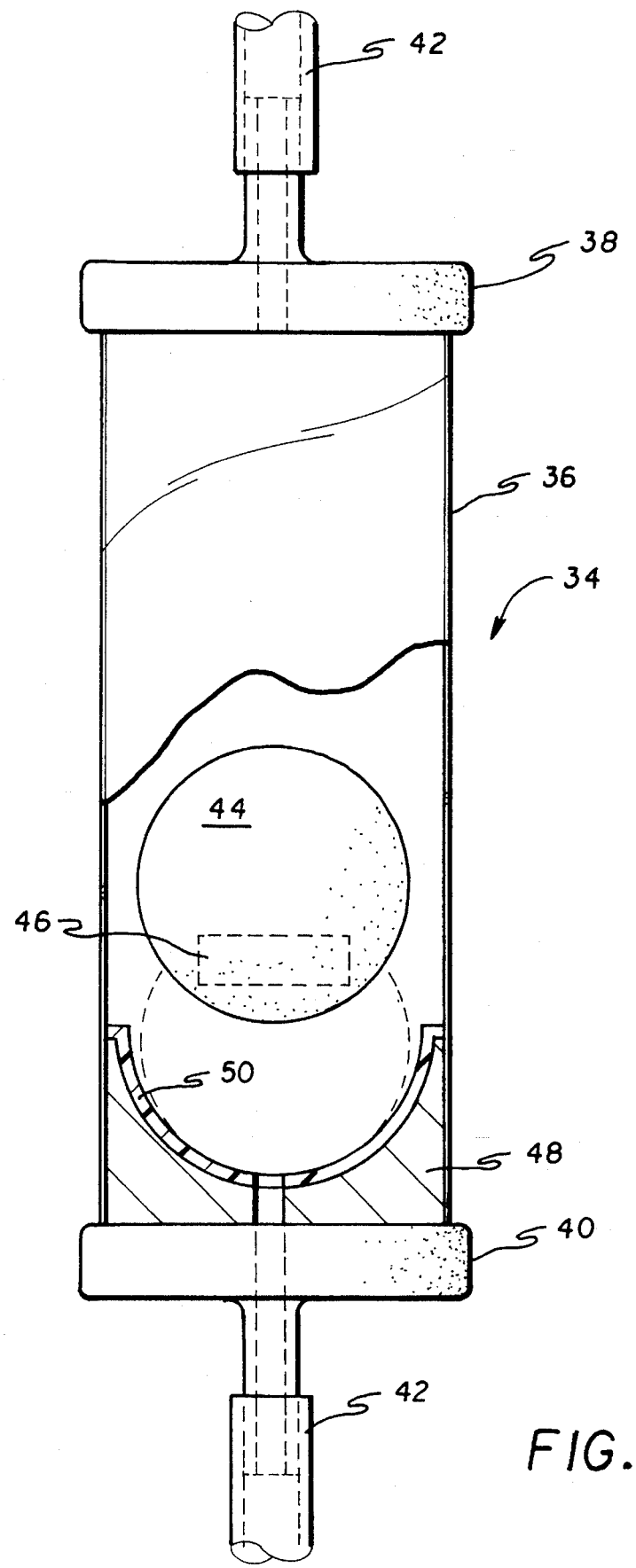
FIG. 3 is a partially sectioned and enlarged scale side view of a second embodiment of a ball valve unit positioned in an IV line having a cup-shaped downstream magnet.

Turning to FIG. 3, a second embodiment of the invention is disclosed wherein the floating in-line ball valve system 34 comprises a cylinder 36 preferably made of a transparent plastic material, e.g., TEFLON™ or a borosilicate glass which is substituted for the tubular mesh cylinder 30 of FIGS. 1 and 2. The upstream end cap or seal 38 and the downstream end cap or seal 40 are ducted and preferably made from silicone rubber and/or plastic. In this embodiment, ball valve assembly 34 is inserted in an intravenous line 42. The floating ball 44 in this embodiment is illustrated as a solid plastic ball containing a magnet 46 positioned at one surface area; alternatively, the floating ball can be hollow as in the previous embodiment. The downstream magnet 48 is cup-shaped and apertured to accept the floating ball 44 containing the upstream magnet 46. Preferably, a thin apertured silicone liner 50 can be employed on the surface of the downstream magnet 48 in order to enhance sealing. The sealing position of ball 52 is illustrated by a dashed outline.

Figure 4:
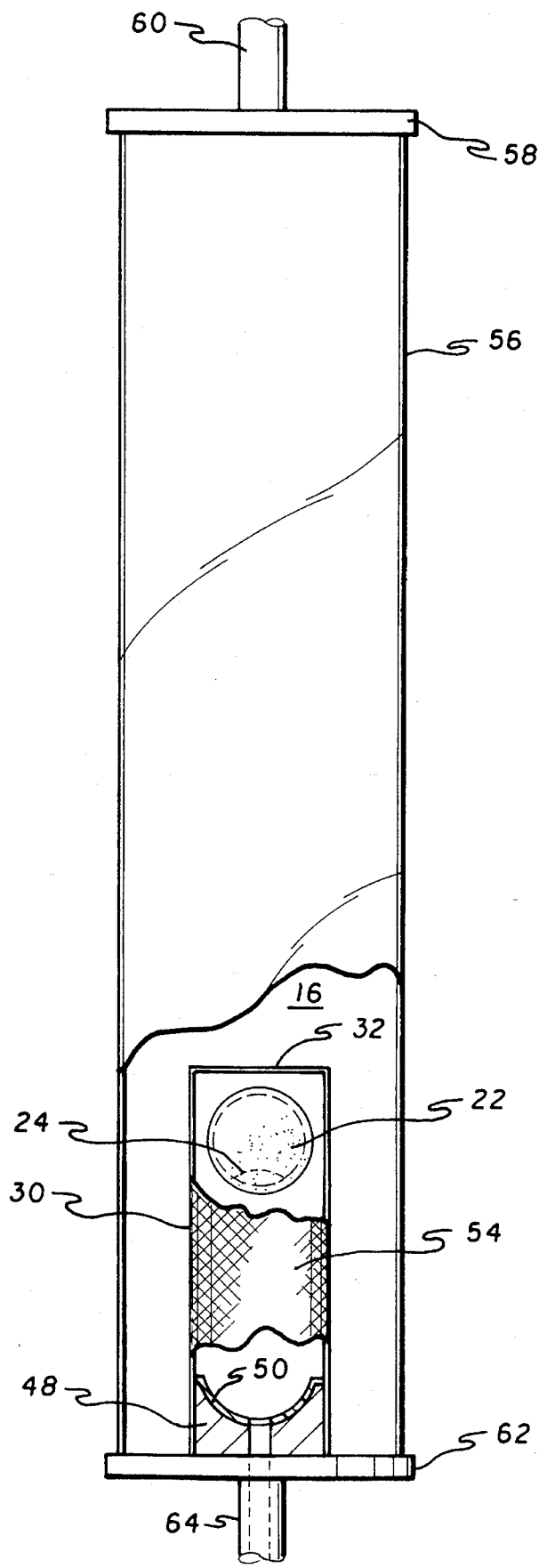
FIG. 4 is a partially sectioned and enlarged scale side view of a third embodiment of a dosage meter containing the gravitational, floating ball valve unit.

The third embodiment illustrated in FIG. 4 involves the insertion of the magnetic, floating ball valve unit or dosage meter assembly 54 in a dosage meter 56 which is inserted in an intravenous line. The hollow ball 22 is encased in an open-meshed tubular cylinder 30 having a cap 32 as seen in FIG. 1. However, the apertured downstream magnet 48 is cup-shaped and has an apertured liner 50 as depicted in FIG. 3. The dosage meter 56 can be of any suitable size. A graduated 150 ml. size dosage meter 56 is illustrated as having a top cap 58 with nipple 60 and a bottom cap 62 with nipple 64. This assembly 54 can be utilized when smaller dosages of an exact volume than that obtainable from an IV bag is desired. It is contemplated that the dosage meter assembly 54, the in-line ball valve assembly 34 of FIG. 3, and/or the IV bag assembly 10 of FIG. 1 can be utilized together if desired in any combination. For example, the combination of the embodiments of FIGS. 1 and 3 can be employed (with the FIG. 3 embodiment located downstream) to advantageously ensure double security against air entrapment. Another example contemplated is the combination of the embodiments of FIGS. 3 and 4, wherein the system of FIG. 3 would be downstream of the dosage meter assembly 54 of FIG. 4.

It should be noted that the selection of a flat or cup-shaped downstream magnet, 28 and 48, respectively, is a matter of choice in any of the embodiments disclosed. A suitable size for the floating ball 22 or 44 can be 6–15 mm. (outside diameter) with the cup-shaped downstream magnet 48 configured to mate with the ball. The upstream floating ball can be made of any inflexible plastic material such as TEFLON™. The magnets can be made from ferritic or ceramic material. The size of the floating magnets 24 and 46 would depend on the viscosity and specific gravity of the body fluid 16 being infused as well as the specific gravity of the balls 22 and 44. Should the magnetic ball seal prematurely, tapping on the valve assembly would dislodge the magnetic ball and allow resumption of the flow.

It is to be understood that the present invention is not limited to the embodiments described above, but encompasses any and all embodiments within the scope of the following claims.

I claim:

1. A gravitational, magnetic, floating ball valve inside a transparent second container for use in the infusion of a fluid into a patient comprising:

a first perforated and hollow cylindrical container having an upstream end and a downstream end, and inserted in an outlet port of a transparent second container;

a first, floating, magnet-containing ball having a predetermined specific gravity, freely positioned within said first perforated and hollow cylindrical container; and a second apertured magnet fixed at said downstream end of said first perforated and hollow cylindrical container; whereby upon infusing a vital fluid into a patient by an intravenous method, said floating magnet containing ball positioned upstream is attracted to said second apertured magnet positioned downstream when the supply of an infusion liquid is near depletion, thereby closing off the supply of fluid to prevent backflow of the infusion liquid and the possible inclusion of air into the body of a patient.

2. The gravitational, magnetic, floating ball valve according to claim 1, wherein said first hollow cylindrical container comprises a transparent tube inserted in an intravenous line.

3. The gravitational, magnetic, floating ball valve according to claim 1, wherein said first hollow and perforated cylindrical container is one of a transparent plastic mesh screen and a stainless steel mesh screen.

4. The gravitational, magnetic, floating ball valve according to claim 3, further in combination with a transparent second fluid container, wherein said second transparent fluid container is an intravenous supply bag.

5. The gravitational, magnetic, floating ball valve according to claim 3, further in combination with a transparent second fluid container, wherein said second transparent fluid container is a dosage meter.

6. The gravitational, magnetic, floating ball valve according to claim 1, wherein said second apertured magnet is flat.

7. The gravitational, magnetic, floating ball valve according to claim 6, wherein said second flat, apertured magnet is encased in a sealing cover.

8. The gravitational, magnetic, floating ball valve according to claim 1, wherein said second apertured magnet is cup-shaped to receive said first magnet-containing floating ball.

9. The gravitational, magnetic, floating ball valve according to claim 8, wherein said second apertured cup-shaped magnet is lined with a thin layer of plastic material.

10. The gravitational, magnetic, floating ball valve according to claim 1, wherein said first magnet-containing floating ball is selected from a solid ball and a hollow ball.

11. The gravitational, magnetic, floating ball valve according to claim 1, wherein said first magnet-containing floating ball is brightly colored to enhance visibility.

12. The gravitational, magnetic, floating ball valve according to claim 1, wherein said ball valve is made of a material that can be autoclaved so that said ball valve can be reused.

13. The gravitational, magnetic, floating ball valve according to claim 1, wherein said ball valve is inserted in an intravenous supply bag, there further being an additional said ball valve and another downstream device selected from a transparent tube and a dosage meter, said additional ball valve being inserted in said another downstream device.

\* \* \* \* \*